*(12)* United States Patent
Andrés-Gil et al.

(10) Patent No.: US 7,462,717 B2
(45) Date of Patent: Dec. 9, 2008

(54) C6- AND C9-SUBSTITUTED CHROMENO[4,3-C]ISOXAZOLINE DERIVATIVES AND THEIR USE AS ANTI-DEPRESSANTS

(75) Inventors: José Ignacio Andrés-Gil, Madrid (ES); Manuel Jesús Alcázar-Vaca, Toledo (ES); Maria Encarnacion Matesanz-Ballesteros, Toledo (ES); Margaretha Henrica Maria Bakker, Alsbach-Haehnlein (DE); Antonius Adrianus Hendrikus Petrus Megens, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 629 days.

(21) Appl. No.: 10/524,989

(22) PCT Filed: Aug. 19, 2003

(86) PCT No.: PCT/EP03/09532

§ 371 (c)(1),
(2), (4) Date: Feb. 18, 2005

(87) PCT Pub. No.: WO2004/018482

PCT Pub. Date: Mar. 4, 2004

(65) Prior Publication Data

US 2006/0122167 A1   Jun. 8, 2006

(30) Foreign Application Priority Data

Aug. 21, 2002   (EP)   ................................. 02078844

(51) Int. Cl.
*A61K 31/55* (2006.01)
*A61K 31/5377* (2006.01)
*A61K 31/496* (2006.01)
*C07D 498/04* (2006.01)
*C07D 413/00* (2006.01)

(52) U.S. Cl. .......................... 544/368; 544/99; 544/137; 544/361; 514/217.1; 514/229.5; 514/232.5; 514/253.03; 514/254.04; 514/293; 514/321; 540/599; 540/603; 546/83; 546/198

(58) Field of Classification Search ............ 514/254.04, 514/293, 321, 217.1, 229.5, 232.5, 253.03; 546/153, 157, 158, 83, 198; 540/599, 603; 544/99, 137, 361, 368
See application file for complete search history.

(56) References Cited

U.S. PATENT DOCUMENTS 7,169,786 B2*  1/2007  Andres-Gil et al. .... 514/253.03
7,265,103 B2*  9/2007  Andres-Gil et al. ...... 514/217.1

FOREIGN PATENT DOCUMENTS

WO   WO 95/07262 A1   3/1995
WO   WO 97/25317 A1   7/1997
WO   WO 02/066484 A1   8/2002

OTHER PUBLICATIONS

International Search Report for PCT/EP03/09532 dated Jan. 23, 2004.

* cited by examiner

*Primary Examiner*—Kamal Saeed
*Assistant Examiner*—Samantha L Shterengarts
(74) *Attorney, Agent, or Firm*—Woodcock Washburn LLP

(57) ABSTRACT

The invention concerns substituted tricyclic isoxazoline derivatives, more in particular tricyclic dihydrobenzopyranoisoxazoline, dihydroquinolinoisoxazoline, dihydronaphthalenoisoxazoline and dihydrobenzothiopyranoisoxazoline derivatives substituted on at least one of the C6- and C9-positions of the phenylpart of the tricyclic moiety with a selected radical, according to Formula (I)

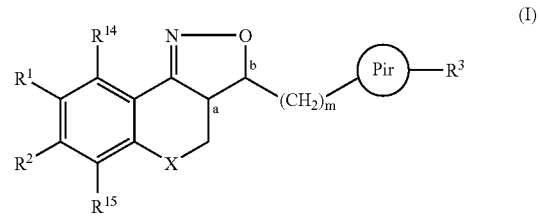

wherein $X=CH_2$, $N-R^7$, S or O, $R^1$, $R^2$, $R^{14}$ and $R^{15}$ are certain specific substituents, with the proviso that at least one of $R^{14}$ and $R^{15}$ is not hydrogen, Pir is preferably an optionally substituted piperidinyl or piperazinyl radical and $R^3$ represents an optionally substituted aromatic homocyclic or heterocyclic ring system including a partially or completely hydrogenated hydrocarbon chain of maximum 6 atoms long with which the ring system is attached to the Pir radical and which may contain one or more heteroatoms selected from the group of O, N and S; a process for their preparation, pharmaceutical compositions comprising them and their use as a medicine, in particular for the treatment of depression, anxiety, movement disorders, psychosis, Parkinson's disease and body weight disorders. The compounds according to the invention have surprisingly been shown to have a serotonine (5-HT) reuptake inhibitor activity in combination with additional $α_2$-adrenoceptor antagonist activity and show a strong anti-depressant activity without being sedative. The invention also relates to novel combination of isoxazoline derivatives according to the invention with one or more other compounds selected from the group of antidepressants, anxiolytics, antipsychotics and anti-Parkinson's disease drugs to improve efficacy and/or onset of action.

11 Claims, No Drawings

C6-AND C9-SUBSTITUTED CHROMENO[4,3-C]ISOXAZOLINE DERIVATIVES AND THEIR USE AS ANTI-DEPRESSANTS

CROSS REFERENCE TO RELATED APPLICATIONS

This application is the national stage of Application No. PCT/EP03/09532, filed Aug. 19, 2003, which application claims priority from EP Patent Application No. 02078844.4 filed Aug. 21, 2002.

The invention concerns substituted tricyclic isoxazoline derivatives, more in particular tricyclic dihydrobenzopyranoisoxazoline, dihydroquinolinoisoxazoline, dihydronaphthalenoisoxazoline and dihydrobenzothiopyranoisoxazoline derivatives substituted on at least one of the C6- and C9-positions of the phenyl part of the tricyclic moiety with a selected radical, as well as processes for their preparation, pharmaceutical compositions comprising them and their use as a medicine, in particular for treating depression, anxiety, movement disorders, psychosis, Parkinson's disease and body weight disorders including anorexia nervosa and bulimia.

The invention also relates to novel combination of said multi-substituted tricyclic isoxazoline derivatives, with anti-depressants, anxiolytics, antipsychotics and anti-Parkinson's disease drugs.

Tetrahydronaphtalene and indane derivatives showing anti-depressant activity are known from EP-361 577 B1. These compounds are typical monoamine reuptake blockers with additional $\alpha_2$-adrenoceptor antagonist activity and they show anti-depressant activity without being sedative.

The problems associated with the compounds according to the state of the art is that the compounds cause considerable side-effects, such as nausea, excitation, an increased heart rate and a reduced sexual function. Furthermore, it requires a long time, in particular 3-4 weeks, before the response starts.

The purpose of the present invention is to provide novel compounds for treating depression, anxiety, movement disorders, psychosis, schizophrenia and body weight disorders, in particular compounds that do not exhibit the aforementioned disadvantages.

The present invention relates to novel substituted tricyclic isoxazoline derivatives according to the general Formula (I)

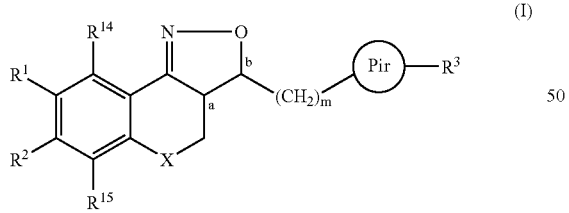

(I)

the pharmaceutically acceptable acid or base addition salts thereof, the stereochemically isomeric forms thereof and the N-oxide form thereof, wherein:

X is $CH_2$, $N-R^7$, S or O;

$R^7$ is selected from the group of hydrogen, alkyl, Ar, Ar-alkyl, alkylcarbonyl, alkyloxycarbonyl and mono- and di(alkyl)aminocarbonyl;

$R^1$, $R^2$, $R^{14}$, $R^{15}$ are each, independently from each other, selected from the group of
hydrogen;
halo;

a radical selected from the group of hydroxy, —$OSO_2H$, —$OSO_2CH_3$, alkyloxy, alkyloxyalkyloxy, alkyloxyalkyloxyalkyloxy, tetrahydrofuranyloxy, alkylcarbonyloxy, alkyloxyalkylcarbonyloxy, pyridinylcarbonyloxy, alkylcarbonyloxyalkyloxy, alkyloxyalkylcarbonyloxyalkyloxy, alkyloxycarbonyloxy, alkenyloxy, alkenylcarbonyloxy, mono- or di(alkyl)aminoalkyloxy, mono- or di(alkyl)aminocarbonyloxyalkyloxy;

a radical selected from the group of cyano, CN—OH, CN-oxyalkyl, alkyl, alkyloxyalkyl, alkyloxyalkyloxyalkyl, alkyloxyalkyloxyalkyloxyalkyl, alkylcarbonylalkyl, alkylcarbonyloxyalkyl, alkyloxycarbonylalkyl, Ar-alkyl, Ar-carbonylalkyl, Ar-oxyalkyl, mono- or di(alkyl)aminoalkyl, mono- or di(alkylcarbonyl)aminoalkyl, mono- or di(alkyl)aminocarbonyl-alkyl, Het-alkyl, formyl, alkylcarbonyl, alkyloxycarbonyl, alkyloxyalkyl-carbonyl, mono- or di(alkyl)aminocarbonyl, Ar-carbonyl and Ar-oxycarbonyl;

—$N$—$R^{10}R^{11}$ wherein $R^{10}$ and $R^{11}$ each, independently from each other, are selected from the group of hydrogen, alkyl, Ar, pyridinyl, Ar-alkyl, pyrrolidinylalkyl, piperidinylalkyl, homopiperidinylalkyl, piperazinylalkyl, morpholinylalkyl, mono- or di(alkyl)aminoalkyl, alkylcarbonyl, alkenylcarbonyl, Ar-carbonyl, pyridinylcarbonyl, alkyloxycarbonyl, mono- or di(alkyl)aminocarbonyl, mono- or di(Ar)aminocarbonyl, mono- or di(alkyloxycarbonylalkyl)aminocarbonyl, pyrrolidinylcarbonyl, aminoiminomethyl, alkylaminoiminomethyl, N-benzylpiperazinyliminomethyl, alkylsulphonyl and Ar-sulphonyl; or $R^{10}$ and $R^{11}$ may be taken together and with the N may form a monovalent radical selected from the group of

(a)

(b)

(c)

(d)

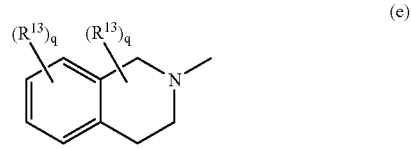

(e)

-continued

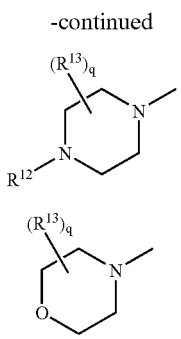

(f)

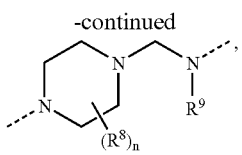

(b)

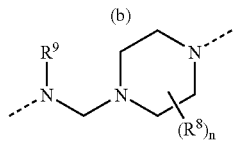

(c)

wherein
$R^{12}$ is selected from the group of hydrogen, alkyl, Ar, Ar-alkyl, Ar-alkenyl, alkylcarbonyl, alkyloxycarbonyl, alkyloxyalkylcarbonyl and mono- or di(alkyl)aminocarbonyl;
each $R^{13}$ is, independently from each other, selected from the group of alkyl, oxo, Ar, Ar-alkyl, Ar-alkenyl and alkyloxycarbonyl;
q is an integer ranging from 0 to 6;
alkylthio;
Ar and Het;
with the proviso that at least one of $R^{14}$ and $R^{15}$ is not hydrogen;
Ar is phenyl or naphthyl, optionally substituted with one or more halo, cyano, oxo, hydroxy, alkyl, formyl, alkyloxy or amino radicals;
Het is a heterocyclic radical selected from the group of $Het^1$, $Het^2$ and $Het^3$;
$Het^1$ is an aliphatic monocyclic heterocyclic radical selected from the group of pyrrolidinyl, dioxolyl, imidazolidinyl, pyrrazolidinyl, piperidinyl, dioxyl, morpholinyl, dithianyl, thiomorpholinyl, piperazinyl and tetrahydrofuryl;
$Het^2$ is a semi-aromatic monocyclic heterocyclic radical selected from the group of 2H-pyrrolyl, pyrrolinyl, imidazolinyl and pyrrazolinyl;
$Het^3$ is an aromatic monocyclic heterocyclic radical selected from the group of pyrrolyl, pyrazolyl, imidazolyl, furyl, thienyl, oxazolyl, isoxazolyl, thiazolyl, isothiazolyl, pyridinyl, pyrimidinyl, pyrazinyl, pyridazinyl and triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl;
wherein each Het-radical may optionally be substituted on either a carbon or heteroatom with halo, hydroxy, alkyloxy, alkyl, Ar, Ar-alkyl, formyl, alkylcarbonyl or pyridinyl;
a and b are asymmetric centers;
$(CH_2)_m$ is a straight hydrocarbon chain of m carbon atoms, m being an integer ranging from 1 to 4;
Pir is a radical according to any one of Formula (IIa), (IIb) or (IIc)

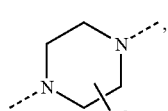

(II)

(a)

optionally substituted with n radicals $R^8$, wherein:
each $R^8$ is, independently from each other, selected from the group of hydroxy, amino, nitro, cyano, halo and alkyl;
n is an integer ranging from 0 to 5;
$R^9$ is selected from the group of hydrogen, alkyl and formyl;
$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;
alkyl represents a straight or branched saturated hydrocarbon radical having from 1 to 6 carbon atoms or a cyclic saturated hydrocarbon radical having from 3 to 6 carbon atoms, optionally substituted with one or more halo, cyano, oxo, hydroxy, formyl or amino radicals and
alkenyl represents a straight or branched unsaturated hydrocarbon radical having one or more double bonds, optionally substituted with one or more halo, cyano, oxo, hydroxy, formyl or amino radicals.

According to the ring numbering system used, radicals $R^1$, $R^2$, $R^{14}$ and $R^{15}$ occupy respectively the C8-, C7-, C9- and C6-positions of the phenylpart of the tricyclic moiety of the isoxazoline derivatives according to the invention.

More in particular, the invention relates to compounds according to Formula (I), the pharmaceutically acceptable acid or base addition salts thereof, the stereochemically isomeric forms thereof and the N-oxide form thereof, wherein $R^3$ is a radical according to any one of Formula (IIIa), (IIIb) or (IIIc)

(III)

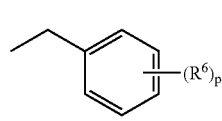

(a)

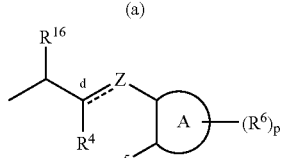

(b)

-continued

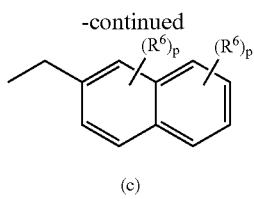

(c)

wherein:
d is a single bond while Z is a bivalent radical selected from the group of —CH$_2$—, —C(=O)—, —CH(OH)—, —C(=N—OH)—, —CH(alkyl)-, —O—, —S—, —S(=O)—, —NH— and —SH—; or d is a double bond while Z is a trivalent radical of formula =CH— or =C(alkyl)-;

A is a 5- or 6-membered aromatic homocyclic or heterocyclic ring, selected from the group of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group of hydrogen, alkyl, Ar, biphenyl, halo and cyano; or $R^4$ and $R^5$ may be taken together to form a bivalent radical —$R^4$—$R^5$— selected from the group of —CH$_2$—, =CH—, —CH$_2$—CH$_2$—, —CH=CH—, —O—, —NH—, =N—, —S—, —CH$_2$N(-alkyl)-, —N(-alkyl)CH$_2$—, —CH$_2$NH—, —NHCH$_2$—, —CH=N—, —N=CH—, —CH$_2$O— and —OCH$_2$—;

each $R^6$ is independently from each other, selected from the group of hydroxy, amino, nitro, cyano, halo, carboxyl, alkyl, Ar, alkyloxy, Ar-oxy, alkyl-carbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$— selected from the group of —CH$_2$—CH$_2$—O—, —O—CH$_2$—CH$_2$—, —O—CH$_2$—C(=O)—, —C(=O)—CH$_2$—O—, —O—CH$_2$—O—, —CH$_2$—O—CH$_2$—, —O—CH$_2$—CH$_2$—O—, —CH=CH—CH=CH—, —CH=CH—CH=N—, —CH=CH—N=CH—, —CH=N—CH=CH—, —N=CH—CH=CH—, —CH$_2$—CH$_2$—CH$_2$—, —CH$_2$—CH$_2$—C(=O)—, —C(=O)—CH$_2$—CH$_2$—, —CH$_2$—C(=O)—CH$_2$— and —CH$_2$—CH$_2$—CH$_2$—CH$_2$— and $R^{16}$ is selected from the group of hydrogen, alkyl, Ar and Ar-alkyl.

Preferably, the invention relates to those compounds according to Formula (I), the pharmaceutically acceptable acid or base addition salts thereof, the stereochemically isomeric forms thereof and the N-oxide form thereof, wherein X=O; m=1; Pir is a radical according to Formula (IIa) wherein n=0; $R^3$ is a radical according to Formula (IIIb) wherein d is a double bond while Z is a trivalent radical of formula =CH—, A is a phenyl ring, $R^4$ is hydrogen or alkyl and $R^5$ and $R^{16}$ are each hydrogen.

More preferably, the invention relates to compounds according to Formula (I), the pharmaceutically acceptable acid or base addition salts thereof, the stereochemically isomeric forms thereof and the N-oxide form thereof, wherein $R^1$, $R^2$, $R^{14}$ and $R^{15}$ are each, independently from each other, selected from the group of hydrogen; halo; cyano; hydroxy; alkyloxy; alkylcarbonyloxyalkyloxy; alkyloxyalkylcarbonyloxyalkyloxy; monoalkylaminocarbonyloxyalkyloxy; morpholinylalkyl; —NR$^{10}$R$^{11}$, wherein R$^{10}$ and R$^{11}$ each, independently from each other, are selected from the group of hydrogen, pyrrolidinylalkyl, mono- or di(alkyl)aminoalkyl, pyridinyl, alkylcarbonyl and phenylalkyl; or R$^{10}$ and R$^{11}$ are taken together to form a radical (a) wherein R$^{13}$ is oxo or a radical (f) wherein R$^{12}$ is hydrogen and q=0; with the proviso that at least one of R$^{14}$ and R$^{15}$ is not hydrogen.

More preferably, the invention relates to compounds according to Formula (I), the pharmaceutically acceptable acid or base addition salts thereof, the stereochemically isomeric forms thereof and the N-oxide form thereof, wherein $R^1$ and $R^2$ are both either hydrogen or methoxy and $R^{14}$ and $R^{15}$ are each, independently from each other, selected from the group of hydrogen; halo; cyano; hydroxy; alkyloxy; alkylcarbonyloxyalkyloxy; alkyloxyalkylcarbonyloxyalkyloxy; monoalkylaminocarbonyloxyalkyloxy; morpholinylalkyl; —NR$^{10}$R$^{11}$, wherein R$^{10}$ and R$^{11}$ each, independently from each other, are selected from the group of hydrogen, pyrrolidinylalkyl, mono- or di(alkyl)aminoalkyl, pyridinyl, alkylcarbonyl and phenylalkyl; or R$^{10}$ and R$^{11}$ are taken together to form a radical (a) wherein R$^{13}$ is oxo or a radical (f) wherein R$^{12}$ is hydrogen and q=0; with the proviso that at least one of R$^{14}$ and R$^{15}$ is not hydrogen.

In the framework of this application, alkyl defines straight or branched saturated hydrocarbon radicals having from 1 to 6 carbon atoms, for example methyl, ethyl, propyl, butyl, 1-methylpropyl, 1,1-dimethylethyl, pentyl, hexyl; or alkyl defines cyclic saturated hydrocarbon radicals having from 3 to 6 carbon atoms, for example cyclopropyl, methylcyclopropyl, cyclobutyl, cyclopentyl and cyclohexyl. The definition of alkyl also comprises alkyl radicals that are substituted with one or more halo, cyano, oxo, hydroxy, formyl or amino radicals, for example hydroxyalkyl, in particular hydroxymethyl and hydroxyethyl and polyhaloalkyl, in particular difluoromethyl and trifluoromethyl.

In the framework of this application, alkenyl represents a straight or branched unsaturated hydrocarbon radical having one or more double bonds, for example ethenyl, 1-propenyl, 2-propenyl and 1,3-butanedienyl. The definition of alkenyl also comprises alkenyl radicals that are substituted with one or more halo, cyano, oxo, hydroxy, formyl or amino radicals, for example hydroxyethenyl.

In the framework of this application, Ar is phenyl or naphthyl, optionally substituted with one or more halo, cyano, oxo, hydroxy, alkyl, formyl, alkyloxy or amino radicals, such as for example, 3-fluoro-phenyl of 3-fluoro-naphthyl.

In the framework of this application, halo is generic to fluoro, chloro, bromo and iodo.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperazinyl radical are N-oxidized.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure, respectively denoted a and b in Formula (I). Due to the synthetic pathway followed for the synthesis of the tricyclic system, the configuration of those two asymmetric centers a and b is predetermined, so that the relative configuration of center a is S* and of center b is R*.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

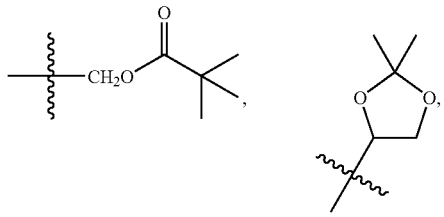

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds according to the invention, in particular compounds according to Formula (I), the pharmaceutically acceptable acid or base addition salts thereof, the stereochemically isomeric forms thereof and the N-oxide form thereof, have surprisingly been shown to have selective serotonine (5-HT) reuptake inhibitor activity in combination with additional α$_2$-adrenoceptor antagonist activity and show a strong anti-depressant and/or anxiolytic activity and/or antipsychotic and/or a body weight control activity without being sedative. Also, in view of their selective serotonin (5-HT) reuptake inhibitor as well as $\alpha_2$-adrenoceptor antagonist activity, compounds according to the invention are also suitable for treatment and/or prophylaxis in diseases where either one of the activities alone or the combination of said activities may be of therapeutic use. In particular, the compounds according to the invention may be suitable for treatment and/or prophylaxis in the following diseases:

Central nervous system disorders, including:
  Mood disorders, including particularly major depressive disorder, depression with or without psychotic features, catatonic features, melancholic features, atypical features of postpartum onset and, in the case of recurrent episodes, with or without seasonal pattern, dysthymic disorder, bipolar I disorder, bipolar II disorder, cyclothymic disorder, recurrent brief depressive disorder, mixed affective disorder, bipolar disorder not otherwise specified, mood disorder due to a general medical condition, substance-induced mood disorder, mood disorder not otherwise specified, seasonal affective disorder and premenstrual dysphoric disorders.
  Anxiety disorders, including panic attack, agoraphobia, panic disorder without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.
  Stress-related disorders associated with depression and/or anxiety, including acute stress reaction, adjustment disorders (brief depressive reaction, prolonged depressive reaction, mixed anxiety and depressive reaction, adjustment disorder with predominant disturbance of other emotions, adjustment disorder with predominant disturbance of conduct, adjustment disorder with mixed disturbance of emotions and conduct, adjustment disorders with other specified predominant symptoms) and other reactions to severe stress.
  Dementia, amnesic disorders and cognitive disorders not otherwise specified, especially dementia caused by degenerative disorders, lesions, trauma, infections, vascular disorders, toxins, anoxia, vitamin deficiency or endocrinic disorders, or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III.
  Cognitive disorders due to cognitive impairment resulting from other medical conditions.
  Personality disorders, including paranoid personality disorder, schizoid personality disorder, schizotypical personality disorder, antisocial personality disorder, borderline personality disorder, histrionic personality disorder, narcissistic personality disorder, avoidant personality disorder, dependent personality disorder, obsessive-compulsive personality disorder and personality disorder not otherwise specified.
  Schizoaffective disorders resulting from various causes, including schizoaffective disorders of the manic type, of the depressive type, of mixed type, paranoid, disorganized, catatonic, undifferentiated and residual schizophrenia, schizophreniform disorder, schizoaffective disorder, delusional disorder, brief psychotic disorder, shared psychotic disorder, substance-induced psychotic disorder and psychotic disorder not otherwise specified.
  Akinesia, akinetic-rigid syndromes, dyskinesia and medication-induced parkinsonism, Gilles de la Tourette syndrome and its symptoms, tremor, chorea, myoclonus, tics and dystonia.
  Attention-deficit/hyperactivity disorder (ADHD).
  Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification.
  Dementia of the Alzheimer's type, with early or late onset, with depressed mood.
  Behavioral disturbances and conduct disorders in dementia and the mentally retarded, including restlessness and agitation.
  Extra-pyramidal movement disorders.
  Down's syndrome.
  Akathisia.
  Eating Disorders, including anorexia nervosa, atypical anorexia nervosa, bulimia nervosa, atypical bulimia nervosa, overeating associated with other psychological disturbances, vomiting associated with other psychological disturbances and non-specified eating disorders.
  AIDS-associated dementia.
Chronic pain conditions, including neuropathic pain, inflammatory pain, cancer pain and post-operative pain following surgery, including dental surgery. These indications might also include acute pain, skeletal muscle pain, low back pain, upper extremity pain, fibromyalgia and myofascial pain syndromes, orofascial pain, abdominal pain, phantom pain, tic douloureux and atypical face pain, nerve root damage and arachnoiditis, geriatric pain, central pain and inflammatory pain.
Neurodegenerative diseases, including Alzheimer's disease, Huntington's chorea, Creutzfeld-Jacob disease, Pick's disease, demyelinating disorders, such as multiple sclerosis and ALS, other neuropathies and neuralgia, multiple sclerosis, amyotropical lateral sclerosis, stroke and head trauma.
Addiction disorders, including:
  Substance dependence or abuse with or without physiological dependence, particularly where the substance is alcohol, amphetamines, amphetamine-like substances, caffeine, cannabis, cocaine, hallucinogens, inhalants, nicotine, opioids, phencyclidine, phencyclidine-like compounds, sedative-hypnotics, benzodiazepines and/or other substances, particularly useful for treating withdrawal from the above substances and alcohol withdrawal delirium.
  Mood disorders induced particularly by alcohol, amphetamines, caffeine, cannabis, cocaine, hallucinogens, inhalants, nicotine, opioids, phencyclidine, sedatives, hypnotics, anxiolitics and other substances.
  Anxiety disorders induced particularly by alcohol, amphetamines, caffeine, cannabis, cocaine, hallucinogens, inhalants, nicotine, opioids, phencyclidine, sedatives, hypnotics, anxiolitics and other substances and adjustment disorders with anxiety.
Smoking cessation.
Body weight control, including obesity.

Sleep disorders and disturbances, including
- Dyssomnias and/or parasomnias as primary sleep disorders, sleep disorders related to another mental disorder, sleep disorder due to a general medical condition and substance-induced sleep disorder.
- Circadian rhythms disorders.
- Improving the quality of sleep.

Sexual dysfunction, including sexual desire disorders, sexual arousal disorders, orgasmic disorders, sexual pain disorders, sexual dysfunction due to a general medical condition, substance-induced sexual dysfunction and sexual dysfunction not otherwise specified.

The present invention thus also relates to compounds according to Formula (I), the pharmaceutically acceptable acid or base addition salts thereof, the stereochemically isomeric forms thereof, the N-oxide form thereof, as well as the prodrugs thereof for use as a medicine, in particular for the treatment and/or prophylaxis of depression, anxiety, movement disorders, psychosis, Parkinson's disease and body weight disorders.

The present invention also relates to a method for the treatment and/or prophylaxis of diseases where either one of the activities (selective serotonine (5-HT) reuptake inhibitor and $\alpha_2$-adrenoceptor antagonist activity) alone or the combination of said activities may be of therapeutic use, in particular for the treatment and/or prophylaxis of depression, anxiety, movement disorders, psychosis, Parkinson's disease and body weight disorders comprising administering to a human in need of such administration an affective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof and the N-oxide form thereof or a prodrug as defined above.

The compounds according to the invention, in particular the compounds according to Formula (I), the pharmaceutically acceptable acid or base addition salts thereof, the stereochemically isomeric forms thereof and the N-oxide form thereof and the prodrugs, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds according to the invention may also be suitable as add-on treatment and/or prophylaxis in the above listed diseases in combination with any combination of compounds selected from the group of antidepressants, anxiolytics, antipsychotics and/or anti-Parkinson's disease drugs which are currently available or in development or which will become available in the future, to improve efficacy and/or onset of action. This is evaluated in rodent models in which antidepressants, anxiolytics, antipsychotics and/or anti-Parkinson's disease drugs are shown to be active. For example, compounds are evaluated in combination with antidepressants, anxiolytics, antipsychotics and/or anti-Parkinson's disease drugs for attenuation of stress-induced hyperthermia.

The invention therefore also relates to a pharmaceutical composition comprising the compounds according to the invention, in particular the compounds according to Formula (I), the pharmaceutically acceptable acid or base addition salts thereof, the stereochemically isomeric forms thereof and the N-oxide form thereof, and the prodrugs and one or more other compounds selected from the group of antidepressants, anxiolytics, antipsychotics and anti-Parkinson's disease drugs.

The invention also relates to the use of a pharmaceutical composition according to the invention for the manufacture of a medicament to improve efficacy and/or onset of action in the treatment and/or prophylaxis of depression, anxiety, movement disorders, psychosis, Parkinson's disease and body weight disorders.

Further, the invention relates to the use of a compound according to the invention for the manufacture of a medicament for the treatment and/or prophylaxis of depression, anxiety, movement disorders, psychosis, Parkinson's disease and body weight disorders, said treatment comprising the simultaneous or sequential administration of a compound according to the invention and one or more other compounds selected from the group of antidepressants, anxiolytics, antipsychosis and anti-Parkinson's drugs. The invention further relates to a process for making a pharmaceutical composition comprising mixing a compound according to the invention, in particular the compounds according to Formula (I), the pharmaceutically acceptable acid or base addition salts thereof, the stereochemically isomeric forms thereof and the N-oxide form thereof, and the prodrugs, or any subgroup thereof and a compound selected from the group of antidepressants, anxiolytics, antipsychotics and anti-Parkinson's disease drugs and a pharmaceutically acceptable carrier.

In vitro receptor and neurotransmitter transporter binding and signal-transduction studies can be used to evaluate the $\alpha_2$-adrenoceptor antagonism activity and serotonine (5-HT) reuptake inhibitor activity of the present compounds. As indices for central penetration and potency to block the $\alpha_2$-adrenoceptors and serotonin transporters, respectively, ex vivo $\alpha_2$-adrenoceptor and serotonin transporter occupancy can be used. As indices of $\alpha2$-adrenoceptor antagonism in vivo, the reversal of the loss of righting reflex, observed in rats after subcutaneous injection or oral dosage of the compound before intravenous medetomidine administration in rats can be used (medetomidine-test). As indices of serotonine (5-HT) reuptake inhibition activity, the inhibition of head-twitches and excitation in rats, observed after subcutaneous injection or oral dosage of the compound before subcutaneous p-chloroamphetamine administration in rats can be used (pCA-test).

The compounds according to the invention can generally be prepared by a succession of steps, each of which is known to the skilled person.

In particular, the compounds according to Formula (I) can be prepared by a nucleophilic substitution reaction with a ring-closed amine, such as a substituted piperazine or piperidine, according to the following reaction:

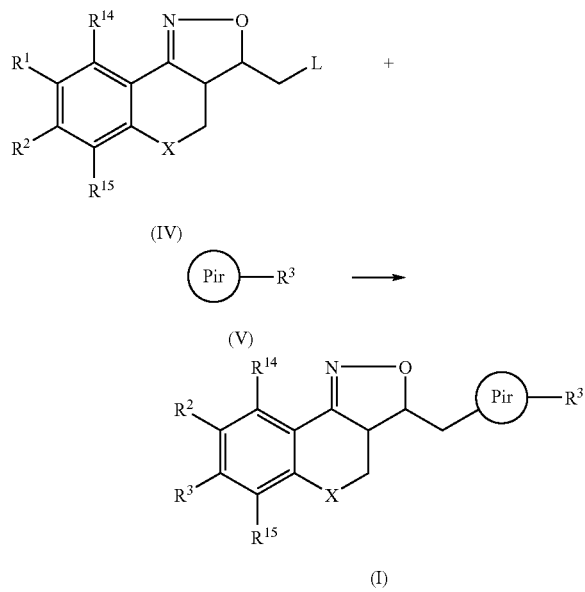

wherein all variables have the same meaning as in Formula (I) and L is any suitable leaving group, such as, for example, halo, in particular chloro, bromo and iodo; sulphonyloxy and 4-methylsulphonyloxy.

The substituents $R^{14}$ and $R^{15}$ in compounds according to Formula (I) may be changed or interconverted into each other by methods well know in the art, such as demethylation, acylation, esterification, metalation followed by electrophilic substitution, amination, amidation, etc.

For example, compounds according to Formula (I) with $R^{14}$ and/or $R^{15}$ being an alkyl or acyl radical can also be prepared from a compound according to Formula (I') in which at $R^{14}$ and/or $R^{15}$ is an halo atom, in particular a bromo atom, using a metalating agent, such as lithium, butyllithyum, etc., under inert atmosphere in the preselce of an inert solvent, for example tetrahydrofuran, and converted into an alkyl or acyl derivative, such as methyl, ethoxycarbonyl, etc. using the corresponding electrophiles, for example, methyl iodide or ethyl carbonate as exemplified in the following reaction scheme where a radical $R^{15}$ is introduced into the molecule on the C6-position.

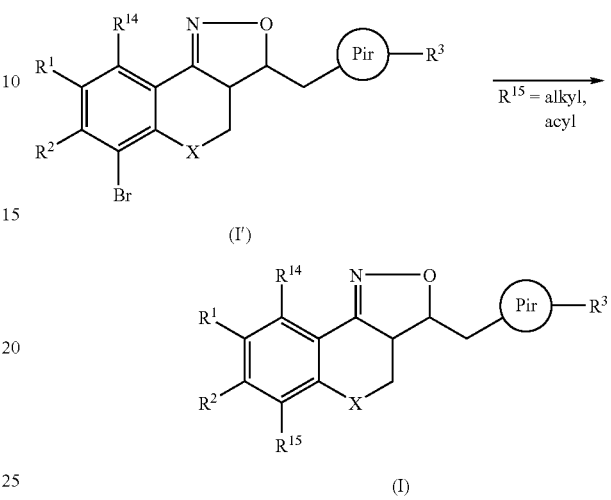

It is self-evident that the same reaction and reaction conditions apply for the introduction of said radicals on the C9-position as $R^{14}$ or on both C6- and C9-positions in the same reaction. In Formula (I'), all variables are defined as in Formula (I).

For example, compounds according to Formula (I) with $R^{14}$ or $R^{15}$ being an amino radical including, for example, morpholine, substituted pyridine or a substituted piperazine, can also be prepared from a compound according to Formula (I') in which at least one of $R^{14}$ and $R^{15}$ is an halo atom, in particular a bromo or iodo atom, by palladium coupling reactions. This art-known reaction is performed on compounds of Formula (I') with nitrogenated compounds of Formula (VI) in the presence of a palladium catalyst such as Pd(2+) salt of acetic acid, Pd(PPh$_3$)$_4$ or Pd$_2$(dba)$_3$, a base, for example K$_2$CO$_3$, Na$_2$CO$_3$, CsCO$_3$ or potassium tert-butoxide, a phosphine, such as PPh$_3$, PBu$_3$ or 2,2'-bis-diphenylphosphanyl-[1,1']binaphthalenyl under an inert atmosphere and in a suitable deoxigenated solvent, such as toluene, dioxane, water, an alcohol, tetrahydrofuran or a mixture thereof, generally at temperatures ranging between 50° C. and 100° C., for example according to the following reaction:

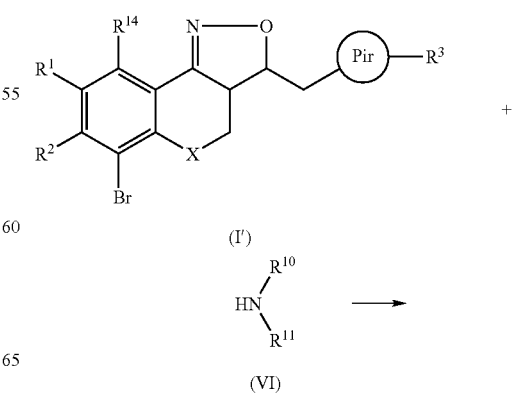

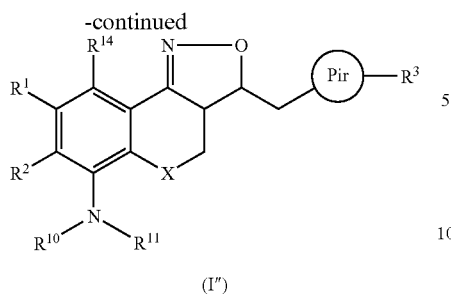

(I″)

It is self-evident that the same reaction and reaction conditions apply for the introduction of said radicals on the C9-position as $R^{14}$ or on both C6- and C9-positions in the same reaction. In Formula (I′), (I″) and (VI), all variables are defined as in Formula (I).

The starting materials and the intermediate compounds are compounds that are either commercially available or may be prepared according to conventional reaction procedures generally known in the art.

The intermediate compounds, in particular the intermediate compounds according to Formula (IV) in which X=O can be prepared according to the following reaction scheme:

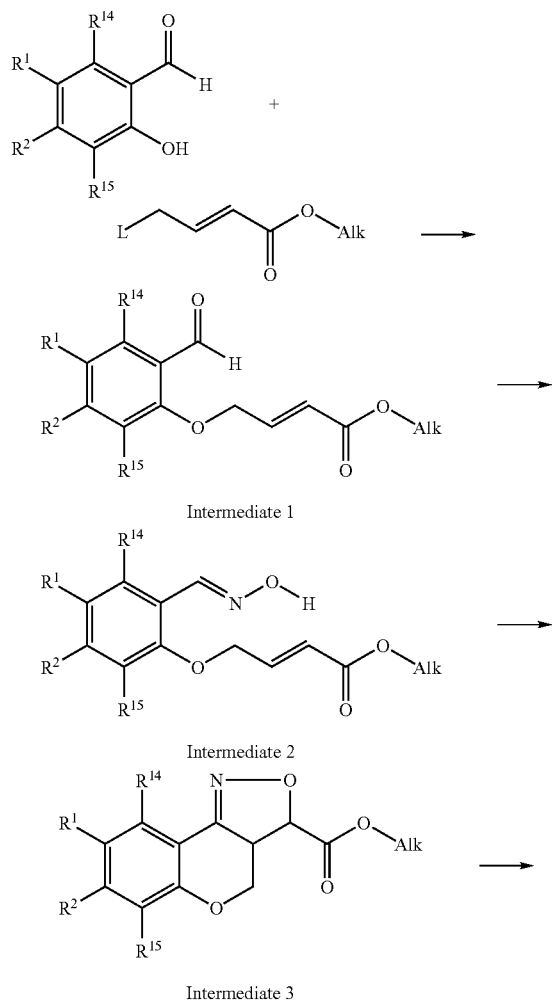

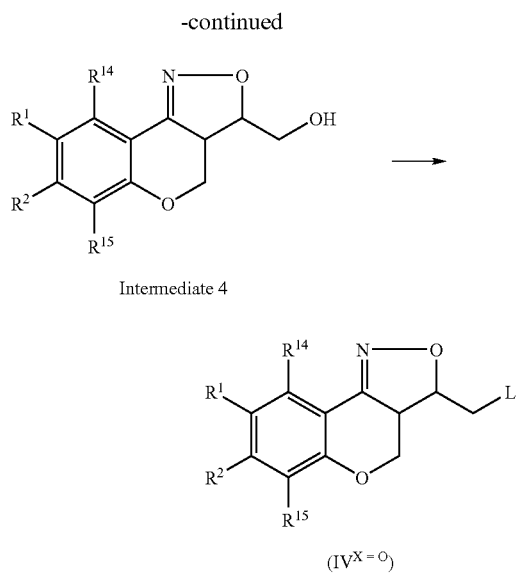

Intermediate 4

($IV^{X=O}$)

Intermediate 1 is converted into an oxime under temperature range –10° C. to 0° C. using art-known techniques, such as hydroxylamine hydrochloride in the presence of a suitable base, such as AcONa, $NaHCO_3$ or pyridine in a reaction inert solvent, for example ethanol. Oxidation of intermediate 2 to its nitrile oxide and in situ intramolecular cycloaddition yields intermediate 3. This oxidation can be carried out using sodium hypochlorite solution in the presence of triethylamine in an inert solvent, such dichloromethane at room temperature. Oxidation can also be performed using chloramine-T hydrate (N-chloro-4-methylbenzenesulphonamide, sodium salt), stirring and heating in a solvent such as refluxing ethanol. At this stage two steroisomers are formed. Reduction of the carbonyl intermediate compound 3 in the presence of a suitable reducing agent, for example sodium borohydride, in a suitable solvent, such as water, alcohol, tetrahydrofuran or a mixture thereof, generally at room temperature yields intermediate compound 4, which can be converted into intermediate compound according to Formula ($IV^{X=O}$) using standard techniques. Thus, reaction with methanesulfonyl chloride or 4-methylbenzenesulfonyl chloride in the presence of a base, such as triethylamine, in a reaction inert solvent, for example dichloromethane, at reaction temperatures ranging between 0° C. and room temperature yields the corresponding sulfonyloxy derivative intermediate according to Formula ($IV^{X=O}$), in which $L=SO_3CH_3$ or $SO_3C_6H_6$—$CH_3$. The corresponding halo-derivative can also be prepared, e.g. treating intermediate according to Formula ($IV^{X=O}$) with triphenylphosphine, in the presence of tetrachloromethane, in a reaction inert solvent, such as tetrahydrofuran, stirring and refluxing the mixture.

In the intermediate compounds according to Formula (IV) prepared according to the previous reaction scheme, at least one of $R^{14}$ and $R^{15}$ may be a halo atom. However, the halo atom may also be introduced using an aromatic bromination reaction, as exemplified in the following reaction scheme for $R^{15}$:

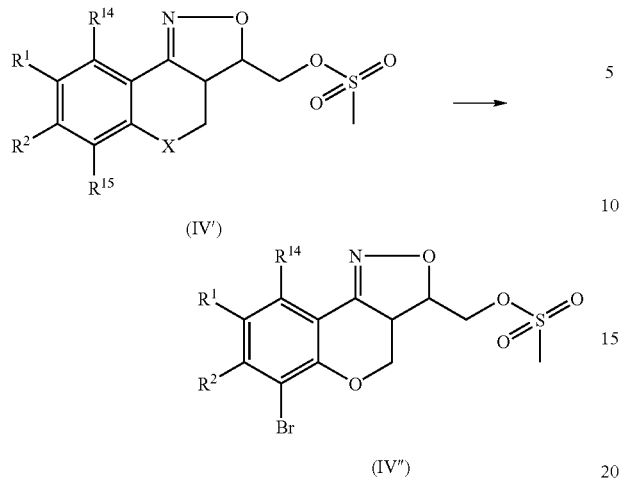

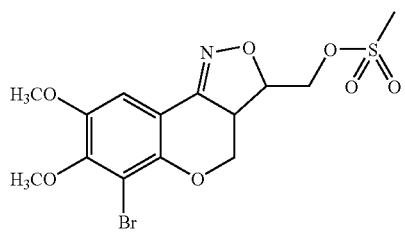

This bromination can be carried out by any brominating agent, such as bromine or N-bromosuccinimide, in a suitable solvent, such us dichloromethane, dioxane or acetonitrile, optionally in the presence of a base, such as, NaHCO$_3$, Na$_2$CO$_3$, triethylamine or pyridine. It is self-evident that the same reaction and reaction conditions apply for a bromination on the C9-position as R$^{14}$ or on both C6- and C9-positions in the same reaction. In Formula (IV') and (IV"), all variables are defined as in Formula (I).

The following examples illustrate the present invention without being limited thereto.

EXPERIMENTAL PART

The carbon ring numbering system for the compounds according to Formula (I) used in this application is as follows

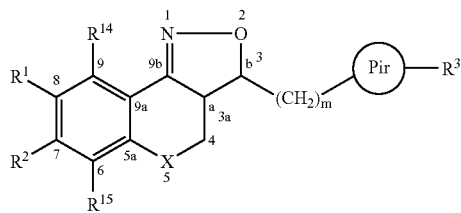

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The stereogenic centers a and b in Formula (I) have respectively the ring numbers 3a and 3.

Hereinafter, "DMF" is defined as N,N-dimethylformamide, "DIPE" is defined as diisopropyl ether, "ACN" is defined as acetonitrile, "DCM" is defined as dichloromethane, "MIK" is defined as 4-methyl-2-pentanone and "THF" is defined as tetrahydrofurane.

A. Preparation of the Intermediate Compounds

Example A.1

Preparation of Intermediate Compound 7 a) A solution of 4-bromo-2-butenoic acid methyl ester (0.1647 mol) in DMF (50 ml) was added dropwise to a mixture of 2-hydroxy-4,5-dimethoxy-benzaldehyde (0.0823 mol) and K$_2$CO$_3$ (0.1647 mol) in DMF (200 ml). The reaction mixture was stirred for 2 hours at room temperature, filtered and the filtrate was evaporated to dryness. The residue was washed in a 10% aqueous NaOH solution, then extracted with CH$_2$Cl$_2$. The separated organic layer was dried (Na$_2$SO$_4$), filtered, and the solvent was evaporated. The residue was washed with diethyl ether, then dried. Yielding: 20 g of intermediate compound 1 (87%).

b) Hydroxylamine (0.045 mol) was added to a solution of intermediate compound 1 (0.041 mol) in ethanol (150 ml). Pyridine (57 ml) was added. The reaction mixture was stirred for 2 hours at room temperature, then poured out into water and acidified with concentrated HCl. This mixture was extracted with CH$_2$Cl$_2$. The separated organic layer was dried (Na$_2$SO$_4$), filtered, and the solvent was evaporated. Yielding: 11.7 g (96%, crude yield). A sample (2 g) was purified by high-performance liquid chromatography over silica gel (eluent: CH$_2$Cl$_2$/CH$_3$OH 95/5). The pure fractions were collected and the solvent was evaporated. The residue was washed with diethyl ether, then dried. Yielding: 0.9 g intermediate compound 2.

c) NaOCl, 5% (130 ml) was added dropwise to a mixture of intermediate compound 2 (0.037 mol) and Et$_3$N (1 ml) in CH$_2$Cl$_2$ (220 ml). The reaction mixture was stirred for 4 hours at room temperature, then washed with water, dried (Na$_2$SO$_4$), filtered, and the filtrate was evaporated. The residue was purified by short open column chromatography over silica gel (eluent: CH$_2$Cl$_2$/2-propanone 100/0 and 95/5). The desired fractions were collected and the solvent was evaporated. Yielding: 5.8 g (54%, used in next traction step without further purification). A sample (2 g) was recrystallised from EtOAc. The precipitate was filtered off and dried. Yielding: 1.7 g of intermediate compound 3.

d) NaBH$_4$ (0.043 mol) was added portionwise to a solution of intermediate compound 3 (0.017 mol) in THF (50 ml) and H$_2$O (5 ml), stirred and cooled on an ice-bath. The resulting reaction mixture was stirred for 2 hours at room temperature. 2-Propanone was added while stirring for 30 min. The reaction mixture was washed with water and extracted with CH$_2$Cl$_2$. The separated organic layer was washed with brine, dried (Na$_2$SO$_4$), filtered and the solvent evaporated. The residue was purified by short open column chromatography over silica gel (eluent: CH$_2$Cl$_2$/CH$_3$OH 95/5) and by high-performance liquid chromatography over silica gel (eluent: CH$_2$Cl$_2$/CH$_3$OH 98/2). The pure fractions were collected and the solvent was evaporated. A sample (1.8 g) was treated with diethyl ether, then dried. Yielding: 1.2 g of intermediate compound 4 (59%).

e) Et$_3$N (0.016 mol) was added to a solution of intermediate compound 4 (prepared according to A3) (0.0109 mol) in CH$_2$Cl$_2$ (60 ml). The mixture was cooled in an ice-bath. Methanesulfonyl chloride (0.012 mol) was added and the resulting reaction mixture was stirred for 30 min. Then, the mixture was washed with water, dried (Na$_2$SO$_4$), filtered and the solvent was evaporated. Yielding: 3.5 g of intermediate compound 5 (82%).

f) Intermediate compound 5 (200 g, 0.58 mol) was separated into its enantiomers by chiral column chromatography over column LC110-2 with stationary phase CHIRALPAK-AD (2000 g, packing pressure: 45 bar, detector range: 2.56, wavelength: 240 nm, temperature: 30° C.; injection solution: 200 g in 8.4 L CH$_3$CN; then, 19.6 L methanol (+2% ethanol) was added, then filtered; injection-volume: 700 ml; eluent: CH$_3$OH/CH$_3$CN 70/30 v/v). Two product fraction groups were collected and their solvent was evaporated. Yield: 95 g of intermediate compound 6.

g) To a mixture of intermediate compound 6 (the B-enantiomer of methanesulfonic acid 7,8-dimethoxy-3a,4-dihydro-3H-chromeno[4,3-c]isoxazol-3-ylmethyl ester) (5 g, 0.01456 mol) and NaHCO$_3$ (1.22 g, 0.0146 mol) in CH$_2$Cl$_2$ (100 ml), in a Parr pressure vessel, was added dropwise Br$_2$ (2.24 ml, 0.043 mol). The resulting reaction mixture was stirred at 50° C. for 2 hours and at room temperature overnight. The crude reaction was washed with water (with sodium thiosulphate) and a saturated NaHCO$_3$ solution and it was extracted with CH$_2$Cl$_2$. The separated organic layer was dried (Na$_2$SO$_4$), filtered and evaporated till dryness. The residue was purified by open column chromatography (eluents: heptane:AcOEt 3/2, CH$_2$Cl$_2$ and CH$_2$Cl$_2$:2-propanone 95/5, 90/10). The pure fractions were collected and the solvent was evaporated. Yielding: 4.32 g (70%) of the B enantiomer of methanesulfonic acid 6-bromo-7,8-dimethoxy-3a,4-dihydro-3H-chromeno[4,3-c]isoxazol-3-ylmethyl ester (intermediate compound 7).

Example A.2

Preparation of Intermediate Compound 12

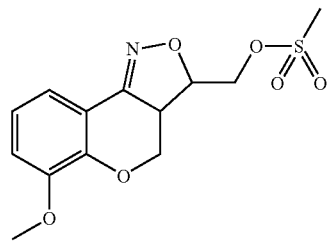

a) To a solution of 2-hydroxy-3-methoxy-benzaldehyde (20 g, 0.1314 mol) in DMF (167 ml) were added K$_2$CO$_3$ (36.33 g, 0.2628 mol) and 4-bromo-2-butenoic acid methyl ester (33.94 ml, 0.1972 mol). The reaction mixture was stirred for 4 hours at room temperature, filtered and the filtrate was evaporated to dryness. The residue was washed with water and it was extracted with AcOEt. The separated organic layer was dried (Na$_2$SO$_4$), filtered, and the solvent was evaporated. The residue was purified by open column chromatography (eluents: CH$_2$Cl$_2$ and CH$_2$Cl$_2$:MeOH 96/4). The pure fractions were collected and the solvent was evaporated. The residue was crystallized from diisopropyl ether, then dried. Yielding: 30.36 g (87%) of 4-(2-formyl-6-methoxy-phenoxy)-but-2-enoic acid ethyl ester (intermediate compound 8).

b) AcONa (4.85 g, 0.059 mol) and hydroxylamine (3.32 g, 0.047 mol) were added to a solution of intermediate compound 8 (10.41 g, 0.039 mol) in ethanol (520 ml), cooling at −20° C. The resulting reaction mixture was stirred for 3 hours at a temperature between −10 and 0° C. The mixture was treated with a 10% citric acid solution, then extracted with AcOEt. The separated organic layer was evaporated and the residue was washed with brine and extracted again with AcOEt. The separated organic layer was dried (Na$_2$SO$_4$), filtered and the solvent was evaporated. Yielding: 16.98 g (quantitative, used in next reaction step, without further purification) of 4-[2-(hydroxyimino-methyl)-6-methoxy-phenoxy]-but-2-enoic acid ethyl ester (intermediate compound 9).

c) NaOCl, 5% (134.26 ml, 0.07878 mol) was added dropwise to a solution of intermediate compound 9 (0.039 mol) in CH$_2$Cl$_2$ (593 ml), stirred and cooled on an ice-bath. The mixture was stirred for 2 hours at room temperature and then it was cooled again with an ice-bath. Et$_3$N (8.23 ml, 0.059 mol) was added dropwise and the resulting reaction mixture was stirred for 2 hours more at room temperature. The crude reaction was washed with water and brine and it was extracted. The separated organic layer was dried (Na$_2$SO$_4$), filtered, and the filtrate was evaporated. The residue was purified by open column chromatography over silica gel (eluent: CH$_2$Cl$_2$/2-propanone 100/0 and 96/4, 90/10). The desired fractions were collected and the solvent was evaporated. Yielding: 7.91 g (73%, used in next reaction step without further purification) of 6-methoxy-3a,4-dihydro-3H-chromeno[4,3-c]isoxazole-3-carboxylic acid ethyl ester (intermediate compound 10).

d) NaBH$_4$ (1.86 g, 0.048 mol) was added portionwise to a solution of intermediate compound 10 (5.36 g, 0.019 mol) in THF (140 ml) and H$_2$O (14 ml), stirred and cooled on an ice-bath. The resulting reaction mixture was stirred for 2 hours at room temperature. The cooled crude reaction was carefully treated with a 10% NH$_4$Cl solution and it was concentrated under vacuo. The mixture was extracted with AcOEt. The separated organic layer was dried (Na$_2$SO$_4$), filtered and the solvent evaporated. Yielding: 4.36 g (95%, used in next reaction step without further purification) of (6-methoxy-3a,4-dihydro-3H-chromeno[4,3-c]isoxazol-3-yl)-methanol (intermediate compound 11).

e) Et$_3$N (5.2 ml, 0.037 mol) was added to a solution of intermediate compound 11 (4.36 g, 0.018 mol) in CH$_2$Cl$_2$ (130 ml). The mixture was cooled with an ice-bath. Methanesulfonyl chloride (0.012 mol) was added and the resulting reaction mixture was stirred for 2 hours. Then, the mixture was washed with water, dried (Na$_2$SO$_4$), filtered and the solvent was evaporated. The reaction was repeated with the residue in order to exhaust the starting material (with 1 equiv. of methanesulfonyl chloride and 1.5 equiv. of Et$_3$N). After 2 hours more of reaction, the mixture was washed with water, dried (Na$_2$SO$_4$), filtered and the solvent was evaporated. Yielding: 6.39 g (quantitative, used in next reaction step without further purification) of methanesulfonic acid 6-methoxy-3a,4-dihydro-3H-chromeno[4,3-c]isoxazol-3-ylmethyl ester (intermediate compound 12).

Example A.3

Preparation of Intermediate Compound 13

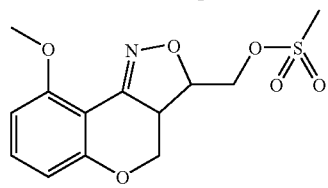

Intermediate compound 13 was produced under the same reaction conditions as exemplified in Example A.2, using 2-hydroxy-6-methoxy-benzaldehyde as starting compound.

B. Preparation of the Final Compounds

Example B.1

Preparation of Final Compound 1

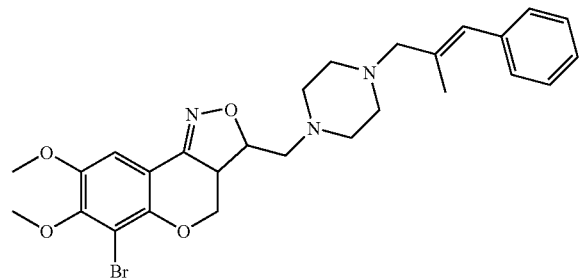

A mixture of intermediate compound 7 (prepared according to example A.1) (4.32 g, 0.01 mol), (E)1-(2-methyl-3-phenyl-2-propenyl)piperazine (3.32 g, 0.015 mol), KI (1.7 g, 0.01 mol) and $K_2CO_3$ (1.41 g, 0.01 mol) in MIK (35 ml) was stirred for ±24 hours at reflux. The crude reaction mixture was washed with water, then extracted with AcOEt. The separated organic layer was dried ($Na_2SO_4$), filtered and the solvent was evaporated. The residue was purified by open column chromatography (eluent: $CH_2Cl_2$:acetone 90/10, 85/15). The pure fractions were collected and the solvent was evaporated. Yielding: 4.64 g (83%) of 6-Bromo-7,8-dimethoxy-3-[4-(2-methyl-3-phenyl-allyl)-piperazin-1-ylmethyl]-3a,4-dihydro-3H-chromeno[4,3-c]isoxazole (final compound 1).

Example B.2

Preparation of Final Compound 2

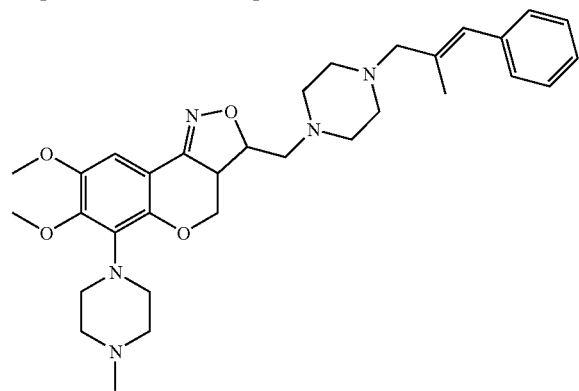

A mixture of final compound 1 (0.2 g, 0.368 mmol), N-methylpiperazine (0.49 ml, 4.4 mmol), $Et_3N$ (0.103 ml, 0.73 mmol) and DMSO (2.5 ml) was stirred at 100° C. for 3 days. The crude reaction was washed with water and extracted with AcOEt. The organic layer was dried ($Na_2SO_4$), filtered and the solvent was evaporated. The residue was purified in a manifold under vacuo with a sep-pak silica cartridge (5 g) eluents: $CH_2Cl_2$:MeOH 100/0 99/1, 96/4. The pure fractions were collected and the solvent was evaporated. Yielding: 22 mg (10%) of 7,8-dimethoxy-3-[4-(2-methyl-3-phenyl-allyl)-piperazin-1-ylmethyl]-6-(4-methyl-piperazin-1-yl)-3a,4-dihydro-3H-chromeno [4,3-c]isoxazole (final compound 2).

Example B.3

Preparation of Final Compound 3

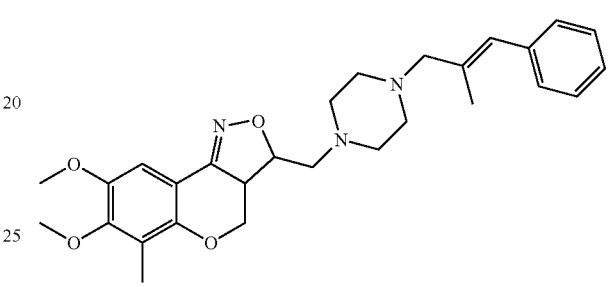

To a solution of final compound 1 (0.5 g, 0.92 mmol) in THF (25 ml), cooled at −78° C. and under $N_2$ atmosphere was added dropwise a solution 2.5 M of n-butyllithium in hexanes (0.66 ml, 1.6 mmol) and the mixture was stirred at −78° C. for 1 hour. Then, methyl iodide (0.3 ml, 4.6 mmol) was added and the resulting reaction mixture was stirred and allowed to warm to room temperature for 1.5 hours. The crude reaction was washed with a 10% $NH_4Cl$ solution and it was extracted with AcOEt. The organic layer was dried ($Na_2SO_4$), filtered and the solvent was evaporated. The residue was purified first, by open column chromatography (eluents: $CH_2Cl_2$:MeOH 99/1, 98/2, 96/4) then, in a manifold under vacuo with a sep-pak silica cartridge (10 g) (eluents: $CH_2Cl_2$:acetone 100/0, 90/10, 100/0 and $CH_2Cl_2$:MeOH 99/1, 98/2, 96/4). The pure fractions were collected and the solvent was evaporated. Yielding: 0.24 g (58%) of 7,8-dimethoxy-6-methyl-3-[4-(2-methyl-3-phenyl-allyl)-piperazin-1-ylmethyl]-3a,4-dihydro-3H-chromeno[4,3-c]isoxazole (final compound 3).

Example B.4

Preparation of Final Compound 4

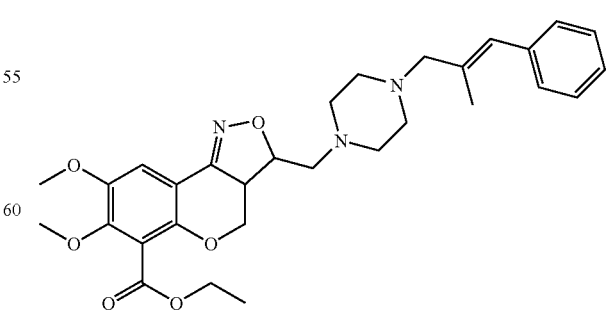

To a solution of final compound 1 (0.6 g, 1.1 mmol) in THF (25 ml), cooled at −78° C. and under $N_2$ atmosphere was added dropwise a solution 2.5 M of n-butyllithium in hexanes (0.66 ml, 1.6 mmol) and the mixture was stirred at −78° C. for 1 hour. Then, diethyl carbonate (0.68 ml, 5.5 mmol) was added and the resulting reaction mixture was stirred and allowed to warm to room temperature for 2 hours. The crude reaction was washed with a 10% NH₄Cl solution and it was extracted with AcOEt. The organic layer was dried (Na₂SO₄), filtered and the solvent was evaporated. The residue was purified first, by open column chromatography (eluents: CH₂Cl₂:acetone 90:10, CH₂Cl₂:MeOH 98/2, 96/4) then, by HPLC (eluent: AcOEt). The pure fractions were collected and the solvent was evaporated. Yielding: 52 mg (8%) of 7,8-dimethoxy-3-[4-(2-methyl-3-phenyl-allyl)-piperazin-1-ylmethyl]-3a,4-dihydro-3H-chromeno[4,3-c]isoxazole-6-carboxylic acid ethyl ester (final compound 4).

Example B.5

Preparation of Final Compound 6

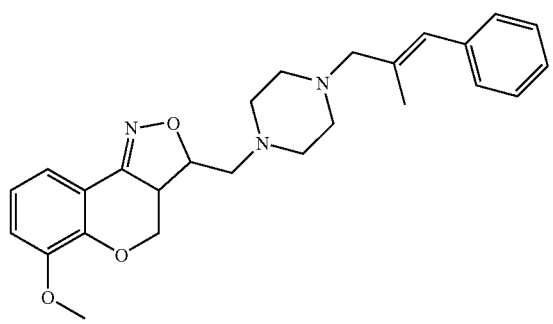

A mixture of intermediate compound 12 (prepared according Example A.2) (0.018 mol), (E)1-(2-methyl-3-phenyl-2-propenyl)piperazine (6.02 g, 0.027 mol), KI (3 g, 0.018 mol) and K₂CO₃ (2.49 g, 0.018 mol) in MIK (90 ml) was stirred for ±24 hours at reflux. The crude reaction mixture was washed with water, then extracted with AcOEt. The separated organic layer was dried (Na₂SO₄), filtered and the solvent was evaporated. The residue was purified by flash column chromatography (eluent: CH₂Cl₂:MeOH 99/1, 98/2, 97/3, 96/4). The pure fractions were collected and the solvent was evaporated. Yielding: 6.5 g (83%) of 6-methoxy-3-[4-(2-methyl-3-phenyl-allyl)-piperazin-1-ylmethyl]-3a,4-dihydro-3H-chromeno[4,3-c]isoxazole (final compound 6).

Example B.6

Preparation of Final Compound 7

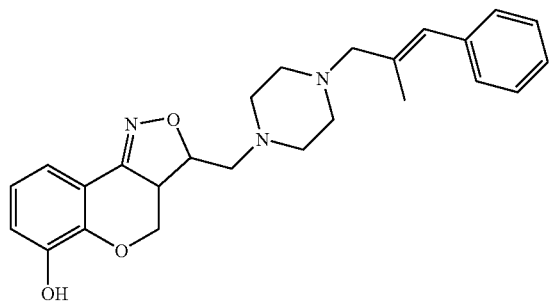

BBr₃ (6.5 ml, 0.068 mol) was added dropwise to a solution of final compound 6 (5.93 g, 0.0136 mol) in CH₂Cl₂ (195 ml), stirred under N₂ atmosphere and cooled with an ice-bath. The resulting reaction mixture was stirred overnight at room temperature. The crude reaction was cooled with an ice-bath and it was carefully treated with a 10% NH₄Cl solution and brine. The mixture was filtered off over celite and the filtrate was extracted with CH₂Cl₂. The separated organic layer was dried (Na₂SO₄), filtered, and the filtrate was evaporated. The residue was purified by open column chromatography over silica gel (eluents: AcOEt:MeOH 100/0, 96/4, CH₂Cl₂:MeOH 96/4 and CH₂Cl₂:MeOH/NH₃ 96/4). The pure fractions were collected and the solvent was evaporated. Yielding: 2.58 g (45%) of 3-[4-(2-methyl-3-phenyl-allyl)-piperazin-1-ylmethyl]-3a,4-dihydro-3H-chromeno[4,3-c]isoxazol-6-ol (final compound 7).

Example B.7

Preparation of Final Compound 21

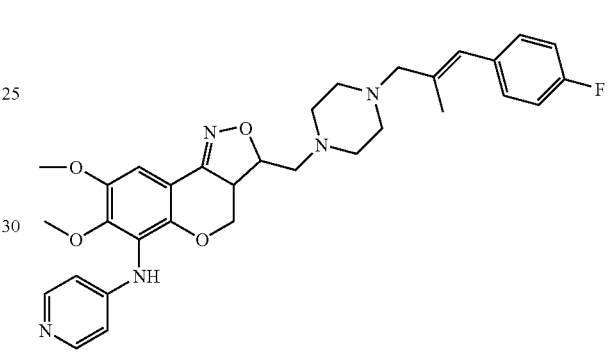

A solution of acetic acid, palladium(2+) salt (0.0026 g) and 2,2'-bis-diphenylphosphanyl-[1,1']binaphthalenyl (0.0000148 mol) in toluene (2 ml) was added to Cs₂CO₃ (0.00046 mol) in a sealed tube under N₂, then a solution of final compound 18 (prepared according to B1) (0.00016 mol) in toluene (2 ml) and finally 4-pyridinamine (0.00039 mol) were added. The reaction mixture was stirred overnight at 100° C. and extra acetic acid, palladium (2+) salt (0.0026 g), 2,2'-bis-diphenylphosphanyl-[1,1']binaphthalenyl (0.0092 g) and 4-pyridinamine (0.037 g) were added at room temperature under N₂. The mixture was stirred over the weekend at 100° C. and again extra acetic acid, palladium (2+) salt (0.0026 g) and 2,2'-bis-diphenylphosphanyl-[1,1']binaphthalenyl (0.0092 g) in DMA (2 ml) were added, then the reaction mixture was stirred overnight at 120° C. under N₂. The mixture was cooled, filtered over celite and the filtrate was evaporated. The residue was purified in a manifold (vac.) using a Sep-Pak silica cartridge (5 g) (eluent: CH₂Cl₂/CH₃OH 98/2, 96/4), then purified by high-performance liquid chromatography (eluent: (0.05% NH₄Oac in H₂O)/CH₃CN). The product fractions were collected and the solvent was evaporated. Yield: 0.0032 g of final compound 21 (3%) (3-{4-[3-(4-fluoro-phenyl)-2-methyl-allyl]-piperazin-1-ylmethyl}-7,8-dimethoxy-3a,4-dihydro-3H-chromeno [4,3-c]isoxazol-6-yl)-pyridin-4-yl-amine The final compounds in Table 1 were made accordingly.

TABLE 1

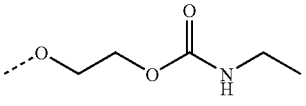

| Co. nr. | Exp. nr. | —R$^1$ | —R$^{14}$ | —R$^{15}$ | —R$^6$ | Phys. data |
|---|---|---|---|---|---|---|
| 1 | B1 | —OCH$_3$ | —H | —Br | —H | B-[3α(E),3aα] |
| 18 | B1 | —OCH$_3$ | —H | —I | —F | [3α(E),3aα] |
| 19 | B3 | —OCH$_3$ | —H | —CN | —F | [3α(E),3aα] |
| 3 | B3 | —OCH$_3$ | —H | —CH$_3$ | —H | B-[3α(E),3aα] |
| 4 | B4 | —OCH$_3$ | —H | —CO$_2$Et | —H | B-[3α(E),3aα]; mp. 60.2-84.3° C. |
| 5 | B4 | —OCH$_3$ | —H | —CO$_2$Me | —H | B-[3α(E),3aα] |
| 6 | B5 | —H | —H | —OCH$_3$ | —H | [3α(E),3aα]; mp. 54.0-62.7° C. |
| 7 | B6 | —H | —H | —OH | —H | [3α(E),3aα]; mp. 119.0-141.9° C. |
| 8 | B5 | —H | —OCH$_3$ | —H | —H | [3α(E),3aα] |
| 9 | B6 | —H | —OH | —H | —H | [3α(E),3aα]; mp. 92.4-117.1° C. |
| 10 | B5 | —H | —H | 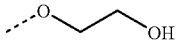 | —H | [3α(E),3aα] |
| 11 | B5 | —H | —H | 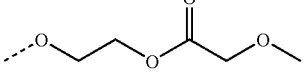 | —H | [3α(E),3aα]; mp. 92.4-117.1° C. |
| 12 | B5 | —H | —H | 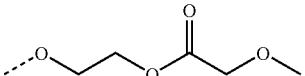 | —H | [3α(E),3aα] |
| 24 | B5 | —H | —H |  | —H | A-[3α(E),3aα] mp. 76.5° C. [α]$^{20}_D$ = −71.6° |
| 25 | B5 | —H | —H |  | —H | B-[3α(E),3aα] mp. 82.4° C. [α]$^{20}_D$ = +72.0° |
| 13 | B5 | —H | —H | 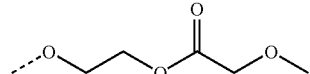 | —H | [3α(E),3aα] |
| 14 | B5 | —H |  | —H | —H | [3α(E),3aα] |
| 15 | B5 | —H | 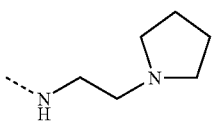 | —H | —H | [3α(E),3aα]; mp. 66.5-78.3° C. |
| 16 | B7 | —H | —H |  | —H | [3α(E),3aα] |

TABLE 1-continued

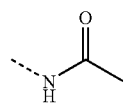

| Co. nr. | Exp. nr. | —R$^1$ | —R$^{14}$ | —R$^{15}$ | —R$^6$ | Phys. data |
|---|---|---|---|---|---|---|
| 22 | B7 | —H | —H | 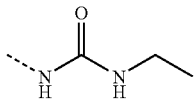 | —H | [3α(E),3aα] |
| 17 | B7 | —H | —H | 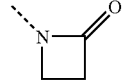 | —H | [3α(E),3aα] |
| 20 | B7 | —OCH$_3$ | —H | 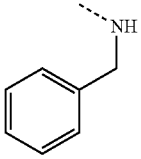 | —F | [3α(E),3aα] |
| 23 | B7 | —H | —H | 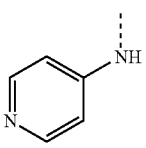 | —H | [3α(E),3aα] |
| 21 | B7 | —OCH$_3$ | —H | 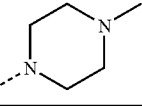 | —F | [3α(E),3aα] |
| 2 | B2 | —OCH$_3$ | —H |  | —H | B-[3α(E),3aα] |

For a number of compounds, melting points were obtained with a Büchi melting point apparatus B-545. The heating medium is a metal block. The melting of the sample is visually observed by a magnifying lense and a big light contrast. Melting points are measured with a temperature gradient of either 3 or 10 degrees Celsius/minute.

C. Pharmacological Examples

Example C1

Binding Experiment for α$_2$-adrenergic Receptor Subtypes and for 5-HTtransporter General The interaction of the compounds of Formula (I) with hα$_2$-receptors and h5-HT-transporters was assessed in in vitro radioligand binding experiments. In general, a low concentration of a radioligand with a high binding affinity for a particular receptor or transporter is incubated with a sample of a tissue preparation enriched in a particular receptor or transporter or with a preparation of cells expressing cloned human receptors in a buffered medium. During the incubation, the radioligand binds to the receptor or transporter. When equilibrium of binding is reached, the receptor bound radioactivity is separated from the non-bound radioactivity, and the receptor- or transporter-bound activity is counted. The interaction of the test compounds with the receptor is assessed in competition binding experiments. Various concentrations of the test compound are added to the incubation mixture containing the receptor- or transporter preparation and the radioligand. The test compound in proportion to its binding affinity and its concentration inhibits binding of the radioligand. The radioligand used for hα$_{2A}$, hα$_{2B}$ and hα$_{2C}$ receptor binding was [$^3$H]-raulwolscine and for the h5-HT transporter was [$^3$H]paroxetine.

Cell Culture and Membrane Preparation.

CHO cells, stabile transfected with human adrenergic-α$_{2A}$-, -α$_{2B}$ or α$_{2C}$ receptor cDNA, were cultured in Dulbecco's Modified Eagle's Medium (DMEM)/Nutrient mixture Ham's F12 (ratio 1:1) (Gibco, Gent-Belgium) supplemented with 10% heat inactivated fetal calf serum (Life Technologies, Merelbeke-Belgium) and antibiotics (100 IU/ml penicillin G, 100 μg/ml streptomycin sulphate, 110 μg/ml pyruvic acid and 100 μg/ml L-glutamine). One day before collection, cells were induced with 5 mM sodiumbutyrate. Upon 80-90% of confluence, cells were scraped in phosphate buffered saline without $Ca^{2+}$ and $Mg^{2+}$ and collected by centrifugation at 1500×g for 10 min. The cells were homogenised in Tris-HCl 50 mM using an Ultraturrax homogenizer and centrifuged for 10 min at 23,500×g. The pellet was washed once by resuspension and rehomogenization and the final pellet was resuspended in Tris-HCl, divided in 1 ml aliquots and stored at −70° C.

Binding Experiment for $\alpha_2$-Adrenergic Receptor Subtypes

Membranes were thawed and re-homogenized in incubation buffer (glycylglycine 25 mM, pH 8.0). In a total volume of 500 μl, 2-10 μg protein was incubated with [$^3$H]raulwolscine (NET-722) (New England Nuclear, USA) (1 nM final concentration) with or without competitor for 60 min at 25° C. followed by rapid filtration over GF/B filter using a Filtermate 196 harvester (Packard, Meriden, Conn.). Filters were rinsed extensively with ice-cold rinsing buffer (Tris-HCl 50 mM pH 7.4). Filter-bound radioactivity was determined by scintillation counting in a Topcount (Packard, Meriden, Conn.) and results were expressed as counts per minute (cpm). Non-specific binding was determined in the presence of 1 μM oxymetazoline for $h\alpha_{2A}$- and $h\alpha_{2B}$-receptors and 1 μM spiroxatrine for $h\alpha_{2C}$ receptors.

Binding Experiment for 5-HT Transporter

Human platelet membranes (Oceanix Biosciences Corporation, Hanover, Md., USA) were thawed, diluted in buffer (Tris-HCl 50 mM, 120 mM NaCl and 5 mM KCl) and quickly (max 3 s) homogenised with an Ultraturrax homogenizer. In a total volume of 250 μL, 50-100 μg protein was incubated with [$^3$H]paroxetine (NET-869) (New England Nuclear, USA) (0.5 nM final concentration) with or without competitor for 60 min at 25° C. Incubation was stopped by rapid filtration of the incubation mixture over GF/B filters, prewetted with 0.1% polyethyleneamine, using a Filtermate 196 harvester (Packard, Meriden, Conn.). Filters were rinsed extensively with ice-cold buffer and radioactivity on the filters was counted in a Topcount liquid scintillation counter (Packard, Meriden, Conn.). Data were expressed as cpm. Imipramine (at 1 μM final concentration) was used to determine the non-specific binding.

Data Analysis and Results

Data from assays in the presence of compound were calculated as a percentage of total binding measured in the absence of test compound. Inhibition curves, plotting percent of total binding versus the log value of the concentration of the test compound, were automatically generated, and sigmoidal inhibition curves were fitted using non-linear regression. The $pIC_{50}$ values of test compounds were derived from individual curves. All compounds according to Formula (I) produced an inhibition at least at the $h\alpha_{2A}$ site (but often also at the $h\alpha_{2B}$ and $h\alpha_{2C}$ sites) and simultaneously at the 5-HT transporter site of more than 50% ($PIC_{50}$) at a test concentration ranging between $10^{-6}$ M and $10^{-9}$ M in a concentration-dependent manner.

TABLE 2

| Co. No | $h\alpha_{2A}$ | $h\alpha_{2B}$ | $h\alpha_{2C}$ | 5-HTT |
|---|---|---|---|---|
| 1 | 8.7 | — | 9.0 | 7.9 |
| 2 | 8.2 | 8.8 | 9.1 | 7.4 |
| 3 | 8.8 | — | 9.4 | 7.5 |
| 4 | 8.2 | 8.4 | 8.9 | 7.2 |
| 5 | 8.7 | 8.3 | 8.9 | 6.8 |
| 6 | 8.1 | 8.7 | 8.8 | 7.3 |

TABLE 2-continued

Pharmacological data.

| Co. No | $h\alpha_{2A}$ | $h\alpha_{2B}$ | $h\alpha_{2C}$ | 5-HTT |
|---|---|---|---|---|
| 7 | 8.1 | 8.9 | 8.7 | 7.3 |
| 8 | 8.7 | 9.0 | 8.6 | 6.6 |
| 9 | 7.6 | 8.7 | 8.9 | 7.2 |
| 10 | 7.1 | 8.3 | 8.2 | 7.4 |
| 11 | 8.5 | 8.6 | 8.5 | 7.3 |
| 12 | 6.9 | 8.2 | 8.4 | 6.9 |
| 14 | 8.6 | 8.5 | 8.9 | 6.0 |
| 15 | 8.4 | 8.4 | 8.6 | 6.7 |
| 16 | 7.4 | 8.4 | 8.1 | 7.6 |
| 17 | 7.2 | 8.2 | 7.8 | 8.0 |
| 18 | 7.6 | 7.5 | 7.6 | 7.3 |
| 19 | 8.0 | 7.7 | 7.8 | 6.9 |
| 20 | 7.1 | 7.6 | 7.5 | 6.9 |
| 21 | 7.2 | 7.8 | 8.2 | 6.4 |
| 22 | 7.5 | 8.7 | 8.4 | 7.6 |
| 23 | 7.2 | 7.3 | 7.7 | 6.9 |
| 24 | 7.0 | 7.6 | 7.4 | 7.5 |
| 25 | 7.4 | 8.8 | 8.7 | 6.5 |

The invention claimed is:

1. A compound according to the general Formula (I)

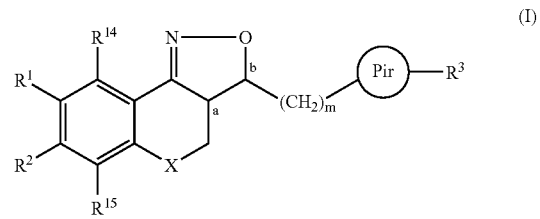

(I)

the pharmaceutically acceptable acid or base addition salts thereof, the stereochemically isomeric forms thereof or the N-oxide form thereof, wherein:

X is $CH_2$, N—$R^7$, S or O;

$R^7$ is selected from the group consisting of hydrogen, alkyl, Ar, Ar-alkyl, alkylcarbonyl, alkyloxycarbonyl and mono- and di(alkyl)aminocarbonyl;

$R^1$, $R^2$, $R^{14}$ $R^{15}$ are each, independently from each other, selected from the group consisting of hydrogen;

halo;

a radical selected from the group consisting of hydroxy, —$OSO_2H$, —$OSO_2CH_3$, alkyloxy, alkyloxyalkyloxy, alkyloxyalkyloxyalkyloxy, tetrahydrofuranyloxy, alkylcarbonyloxy, alkyloxyalkylcarbonyloxy, pyridinylcarbonyloxy, alkylcarbonyloxyalkyloxy, alkyloxyalkylcarbonyloxyalkyloxy, alkyloxycarbonyloxy, alkenyloxy, alkenylcarbonyloxy, mono- or di(alkyl)aminoalkyloxy, mono- or di(alkyl)aminocarbonyloxyalkyloxy;

a radical selected from the group consisting of cyano, CN—OH, CN-oxyalkyl, alkyl, alkyloxyalkyl, alkyloxyalkyloxyalkyl, alkyloxyalkyloxyalkyloxyalkyl, alkylcarbonylalkyl, alkylcarbonyloxyalkyl, alkyloxycarbonylalkyl, Ar-alkyl, Arcarbonylalkyl, Ar-oxyalkyl, mono- or di(alkyl)aminoalkyl, mono- or di(alkylcarbonyl)aminoalkyl, mono- or di(alkyl)aminocarbonylalkyl, Het-alkyl, formyl, alkylcarbonyl, alkyloxycarbonyl, alkyloxyalkylcarbonyl, mono- or di(alkyl)aminocarbonyl, Ar-carbonyl and Ar-oxycarbonyl;

—N—$R^{10}R^{11}$ wherein $R^{10}$ and $R^{11}$ each, independently from each other, are selected from the group consisting of hydrogen, alkyl, Ar, pyridinyl, Ar-alkyl, pyrrolidinylalkyl, piperidinylalkyl, homopiperidinylalkyl, piperazinylalkyl, morpholinylalkyl, mono- or di(alkyl)aminoalkyl, alkylcarbonyl, alkenylcarbonyl, Ar-carbonyl, pyridinylcarbonyl, alkyloxycarbonyl, mono- or di(alkyl)aminocarbonyl, mono- or di(Ar)aminocarbonyl, mono- or di(alkyloxycarbonylalkyl)aminocarbonyl, pyrrolidinylcarbonyl, aminoiminomethyl, alkylaminoiminomethyl, N-benzylpiperazinyliminomethyl, alkylsulphonyl and Ar-sulphonyl; or $R^{10}$ and $R^{11}$ may be taken together and with the N may form a monovalent radical selected from the group consisting of

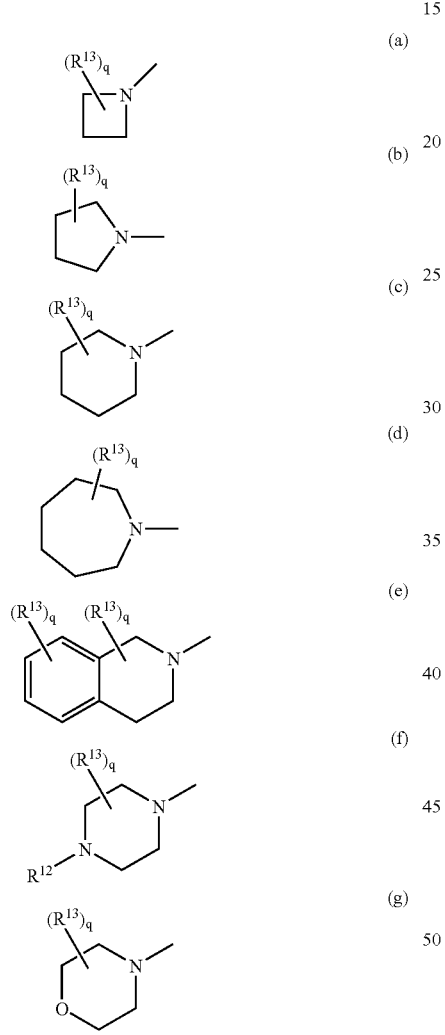

wherein:
$R^{12}$ is selected from the group consisting of hydrogen, alkyl, Ar, Ar-alkyl, Ar-alkenyl, alkylcarbonyl, alkyloxycarbonyl, alkyloxyalkylcarbonyl and mono- or di(alkyl)aminocarbonyl;

each $R^{13}$ is, independently from each other, selected from the group consisting of alkyl, oxo, Ar, Ar-alkyl, Ar-alkenyl and alkyloxycarbonyl;

q is an integer ranging from 0 to 6;
alkylthio;
Ar and Het;
with the provisio that at least one of $R^{14}$ and $R^{15}$ is not hydrogen;

Ar is phenyl or naphthyl, optionally substituted with one or more halo, cyano, oxo, hydroxy, alkyl, formyl, alkyloxy or amino radicals;

Het is a heterocyclic radical selected from the group consisting of $Het^1$, $Het^2$ and $Het^3$;

$Het^1$ is an aliphatic monocyclic heterocyclic radical selected from the group consisting of pyrrolidinyl, dioxolyl, imidazolidinyl, pyrrazolidinyl, piperidinyl, dioxyl, morpholinyl, dithianyl, thiomorpholinyl, piperazinyl and tetrahydrofuryl;

$Het^2$ is a semi-aromatic monocyclic heterocyclic radical selected from the group consisting of 2H-pyrrolyl, pyrrolinyl, imidazolinyl and pyrrazolinyl;

$Het^3$ is an aromatic monocyclic heterocyclic radical selected from the group consisting of pyrrolyl, pyrazolyl, imidazolyl, furyl, thienyl, oxazolyl, isoxazolyl, thiazolyl, isothiazolyl, pyridinyl, pyrimidinyl, pyrazinyl, pyridazinyl and triazinyl; or an aromatic bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl and benzothienyl; wherein each Het-radical may optionally be substituted on either a carbon or heteroatom with halo, hydroxy, alkyloxy, alkyl, Ar, Ar-alkyl, formyl, alkylcarbonyl or pyridinyl;

a and b are asymmetric centers;
$(CH_2)_m$ is a straight hydrocarbon chain of m carbon atoms, m being an integer ranging from 1 to 4;

Pir is a radical according to any one of Formula (IIa), (IIb) or (IIc)

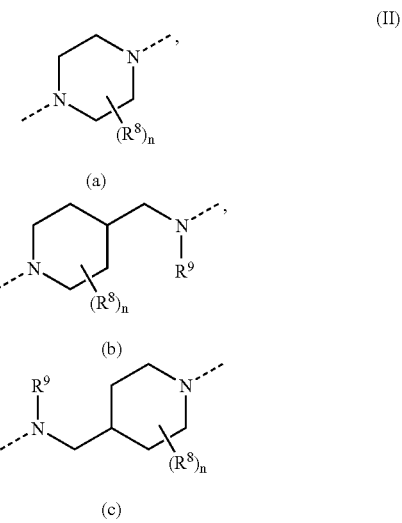

(II)

optionally substituted with n radicals $R^8$, wherein
each R is independently from each other, selected from the group consisting of hydroxy, amino, nitro, cyano, halo and alkyl;

n is an integer ranging from 0 to 5;
$R^9$ is selected from the group consisting of hydrogen, alkyl and formyl;

$R^3$ represents an optionally substituted aromatic homocyclic or heterocyclic ring system together with an optionally substituted and partially or completely hydrogenated hydrocarbon chain of 1 to 6 atoms long with which said ring system is attached to the Pir radical and of which may contain one or more heteroatoms selected from the group of O, N and S;

alkyl represents a straight or branched saturated hydrocarbon radical having from 1 to 6 carbon atoms or a cyclic saturated hydrocarbon radical having from 3 to 6 carbon atoms, optionally substituted with one or more halo, cyano, oxo, hydroxy, formyl or amino radicals and alkenyl represents a straight or branched unsaturated hydrocarbon radical having one or more double bonds, optionally substituted with one or more halo, cyano, oxo, hydroxy, formyl or amino radicals.

2. The compound according to claim 1, wherein
$R^3$ is a radical according to any one of Formula (IIIa), (IIIb) or (IIIc)

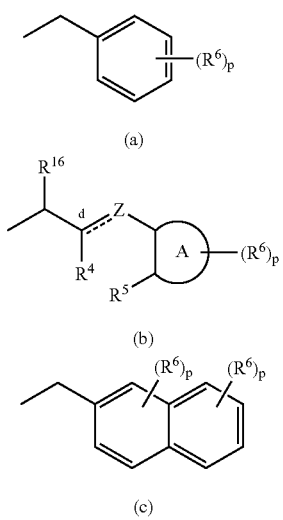

(III)

(a)

(b)

(c)

wherein:
d is a single bond while Z is a bivalent radical selected from the group consisting of —$CH_2$—, —C(=O)—, —CH(OH)—, —C(=N—OH)—, —CH(alkyl)-, —O—, —S—, —S(=O)—, —NH— and —SH—; or d is a double bond while Z is a trivalent radical of formula =CH— or =C(alkyl)-;

A is a 5- or 6-membered aromatic homocyclic or heterocyclic ring, selected from the group consisting of phenyl, pyranyl, pyridinyl, pyrazinyl, pyrimidinyl, pyridazinyl, thienyl, isothiazolyl, pyrrolyl, imidazolyl, pyrazolyl, furanyl, oxadiazolyl and isoxazolyl;

p is an integer ranging from 0 to 6;

$R^4$ and $R^5$ are each, independently from each other, selected from the group consisting of hydrogen, alkyl, Ar, biphenyl, halo and cyano; or $R^4$ and $R^5$ may be taken together to form a bivalent radical —$R^4$—$R^5$— selected from the group consisting of —$CH_2$—, =CH—, —$CH_2$—$CH_2$—, —CH=CH—, —O—, —NH—, =N—, —S—, —$CH_2$N(-alkyl)-, —N(-alkyl)$CH_2$—, —$CH_2$NH—, —NHCH$_2$—, —CH=N—, —N=CH—, —$CH_2$O— and —O$CH_2$—;

each $R^6$ is independently from each other, selected from the group consisting of hydroxy, amino, nitro, cyano, halo, carboxyl, alkyl, Ar, alkyloxy, Ar-oxy, alkylcarbonyloxy, alkyloxycarbonyl, alkylthio, mono- and di(alkyl)amino, alkylcarbonylamino, mono- and di(alkyl)aminocarbonyl, mono- and di(alkyl)aminocarbonyloxy, mono- and di(alkyl)aminoalkyloxy; or two vicinal radicals $R^6$ may be taken together to form a bivalent radical —$R^6$—$R^6$— selected from the group consisting of —$CH_2$—$CH_2$—O—, —O—$CH_2$—$CH_2$—, —O—$CH_2$—C(=O)—, —C(=O)—$CH_2$—O—, —O—$CH_2$—O—, —$CH_2$—O—$CH_2$—, —O—$CH_2$—$CH_2$—O—, —CH=CH—CH=CH—, —CH=CH—CH=N—, —CH=CH—N=CH—, —CH=N—CH=CH—, —N=CH—CH=CH—, —$CH_2$—$CH_2$—$CH_2$—, —$CH_2$—$CH_2$—C(=O)—, —C(=O)—$CH_2$—$CH_2$—, —$CH_2$—C(=O)—$CH_2$— and —$CH_2$—$CH_2$—$CH_2$—$CH_2$— and $R^{16}$ is selected from the group consisting of hydrogen, alkyl, Ar and Ar-alkyl.

3. A compound according to claim 2, wherein X=O; m=1; Pir is a radical according to Formula (IIa) wherein n=0; $R^3$ is a radical according to Formula (IIIb) wherein d is a double bond while Z is a trivalent radical of formula =CH—, A is a phenyl ring, $R^4$ is hydrogen or alkyl and $R^5$ and $R^{16}$ are each hydrogen.

4. A compound according to claim 1, wherein, $R^1$, $R^2$, $R^{14}$ and $R^{15}$ are each, independently from each other, selected from the group consisting of hydrogen; halo; cyano; hydroxy; alkyloxy; alkylcarbonyloxyalkyloxy; alkyloxyalkylcarbonyloxyalkyloxy; monoalkylaminocarbonyloxyalkyloxy; morpholinylalkyl; —$NR^{10}R^{11}$, wherein $R^{10}$ and $R^{11}$ each, independently from each other, are selected from the group consisting of hydrogen, pyrrolidinylalkyl, mono- or di(alkyl)aminoalkyl, pyridinyl, alkylcarbonyl and phenylalkyl; or $R^{10}$ and $R^{11}$ are taken together to form a radical (a) wherein $R^{13}$ is oxo or a radical (f) wherein $R^{12}$ is hydrogen and q=0; with the provisio that at least one of $R^{14}$ and $R^{15}$ is not hydrogen.

5. A compound according to claim 1, wherein $R^1$ and $R^2$ are both either hydrogen or methoxy and $R^{14}$ and $R^{15}$ are each, independently from each other, selected from the group consisting of hydrogen; halo; cyano; hydroxy; alkyloxy; alkylcarbonyloxyalkyloxy; alkyloxyalkylcarbonyloxyalkyloxy; monoalkylaminocarbonyloxyalkyloxy; morpholinylalkyl; —$NR^{10}R^{11}$, wherein $R^{10}$ and $R^{11}$ each, independently from each other, are selected from the group consisting of hydrogen, pyrrolidinylalkyl, mono- or di(alkyl)aminoalkyl, pyridinyl, alkylcarbonyl and phenylalkyl; or $R^{10}$ and $R^{11}$ are taken together to form a radical (a) wherein $R^{13}$ is oxo or a radical (f) wherein $R^{12}$ is hydrogen and q=0; with the provisio that at least one of $R^{14}$ and $R^{15}$ is not hydrogen.

6. A method for treating depression, anxiety, movement disorders, and/or Parkinson's disease in a mammal comprising administering to the mammal a therapeutically effective amount of a compound according to claim 1.

7. A pharmaceutical composition comprising a pharmaceutically acceptable carrier and, as active ingredient a therapeutically effective amount of a compound according to claim 1.

8. A process for making a pharmaceutical composition comprising mixing a compound according to claim 1 and a pharmaceutically acceptable carrier.

9. A pharmaceutical composition comprising a pharmaceutically acceptable carrier and, as active ingredient a therapeutically effective amount of a compound according to claim 1 and one or more other compounds selected from the group consisting of antidepressants, anxiolytics, anti-psychotics and anti-Parkinson's disease drugs.

10. A method of treatment of depression, anxiety, movement disorders, and/or Parkinson's disease, said treatment comprising the simultaneous or sequential administering of a compound according to claim 1 and one or more other compounds selected from the group consisting of antidepressants, anxiolytics, antipsychotics and anti-Parkinson's drugs.

11. A process for making a pharmaceutical composition comprising mixing a compound according to claim 1 and a compound selected from the group consisting of antidepressants, anxiolytics, antipsychotics and anti-Parkinson's disease drugs and a pharmaceutically acceptable carrier.

* * * * *